United States Patent
Aeschbach et al.

(10) Patent No.: US 6,309,652 B1
(45) Date of Patent: Oct. 30, 2001

(54) EXTRACTION OF OLIVES FOR OBTAINING ANTIOXIDANT COMPOSITIONS

(75) Inventors: Robert Aeschbach; Umberto Bracco, both of Vevey; Patricia Rossi, La Tour-De-Peilz, all of (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/194,959

(22) PCT Filed: Jun. 4, 1997

(86) PCT No.: PCT/EP97/02967

§ 371 Date: Jun. 7, 1999

§ 102(e) Date: Jun. 7, 1999

(87) PCT Pub. No.: WO97/47711

PCT Pub. Date: Dec. 18, 1997

(30) Foreign Application Priority Data

Jun. 8, 1996 (EP) .................................................. 96201590

(51) Int. Cl.⁷ ...................................................... A61K 7/00
(52) U.S. Cl. .......................... 424/401; 424/439; 424/725; 424/777; 426/541; 426/542; 514/557; 514/724; 514/783
(58) Field of Search ................................ 424/195.1, 439, 424/401, 725, 777; 426/541, 542, 384, 385; 574/557, 558, 578, 724, 783

(56) References Cited

U.S. PATENT DOCUMENTS 4,844,902 * 7/1989 Grohe .................................... 424/449
5,585,130   12/1996 Aeschbach et al. .................. 426/542
5,795,609   8/1998 Aeschbach et al. .................. 426/542

FOREIGN PATENT DOCUMENTS

0686353 * 12/1995 (EP) .
93/11567 * 9/1993 (WO) .

OTHER PUBLICATIONS

Brenes et al J. Agric. Food Chem. 43, pp. 2702–2708, 1995.*

Bianchi et al Phyto Chemistry vol. 35 #5 pp. 1335–37, 1994.*

Roncero Renue Francaise der Cores Grao 25 #1, 1978.*

* cited by examiner

*Primary Examiner*—Neil S. Levy
(74) *Attorney, Agent, or Firm*—Vogt & O'Donnell, LLP

(57) ABSTRACT

Antioxidant compositions for protecting food and cosmetic products from oxidation are isolated from olives by grinding olives to obtain ground olive material which then is dried and then the dried material is pressed which provides for recovering and obtaining, from the pressing, a lipid composition separate from a pressed olive cake, the lipid composition containing lipid-soluble and water-soluble antioxidants. Additionally, further treatment of the cake material by combining a medium chain triglyceride, glycol, or a $C_2$–$C_6$ alkyleneglycol with the cake material and then pressing under a pressure of at least 40 bar provides for recovering and obtaining water-soluble antioxidants from the cake material.

20 Claims, No Drawings

EXTRACTION OF OLIVES FOR OBTAINING ANTIOXIDANT COMPOSITIONS

CROSS REFERENCE TO RELATED APPLICATION

This is a national stage application of International Patent Application No. PCT/EP97/02967 filed Jun. 4, 1997.

BACKGROUND OF THE INVENTION

The present invention relates to antioxidant compositions for use in such as food and cosmetic products to protect the food and cosmetic products from oxidation and to processes for obtaining such antioxidant compositions, and more particularly, the present invention relates to obtaining antioxidant compositions from olives.

In a conventional process, olives are treated by pressing and three phases are obtained: an aqueous phase, a lipid phase and a solid phase. In such a process, the aqueous phase and the solid phase are removed. Water-soluble antioxidants are thus lost in the solid phase and also in the aqueous phase. Furthermore, these antioxidants are so dilute in the aqueous phase that even if it were desired, they could no longer be recovered.

Moreover, the aqueous phase, whose volume is approximately four times greater than the volume of the lipid phase, has to be treated in a sewage treatment plant as waste water.

Thus, A. Uzzan (Manuel des corps gras—ISBN 2-85206-662/9—1992—763–768) describes in particular a process for producing olive oil by pressing, in which the olives are cleaned, worked and then passed into a hydraulic press so as to separate the liquid phase and the solid phase. At this stage, the liquid phase is divided by decantation or by centrifugation into its two constituents: the aqueous phase containing the water-soluble substances in the olive and the olive oil. These two constituents are once again centrifuged so as, on the one hand, to collect the clarified and purified oil and, on the other hand, to extract the residual oil contained in the aqueous phase. This aqueous phase as well as the previous solid phase, which are still rich in antioxidants, are removed.

SUMMARY OF THE INVENTION

The aim of the present invention is to provide a process which makes it possible to recover, from green olives and/or from ripe olives, that is to say at various degrees of maturity, on the one hand, a lipid fraction enriched with antioxidants and, on the other hand, an extract enriched with antioxidants.

To this, in the process for extracting antioxidants from olives according to the invention: olives are ground, the ground olives are dried under vacuum so as to obtain dried olives rich in water-soluble antioxidants, the dried olives are pressed so as to recover a lipid fraction enriched with antioxidants and an oil cake, at least one extraction is performed on the oil cake at high temperature with MCT, that is to say a mixture of medium-chain triglycerides, or with a $C_2$–$C_6$ alkyleneglycol using a pressure greater than or equal to 40 bar, and then an extract enriched with antioxidants is recovered from the oil cake.

It has been observed, surprisingly, that such a process effectively makes it possible to obtain a lipid fraction and an extract enriched with antioxidants and, more particularly, with water-soluble antioxidants. Furthermore, on account of the fact that there is no waste water, the process according to the present invention has obvious ecological advantages.

Further, the present invention provides a lipid fraction composition containing antioxidants which has induction time of 15–75 h at a temperature of 110–120° C.

In carrying out the process of the present invention, the olives may, for example, be chosen from green olives and/or ripe olives.

The olives may, for example, be frozen so as to facilitate grinding.

To accomplish the grinding customary techniques for grinding stone fruits are used, especially hammer, disc, colloidal or molasses mills or a blade cutter.

The ground olives may be treated enzymatically with the aid of enzymes of bacterial or fungal origin, by hydrolases, glucosidases or polyphenolhydrolases, for example, so as to hydrolyse the glycosides and enhance the extraction of the antioxidants, for example.

The ground olives may be dried under vacuum at a temperature less than or equal to 80° C., so as to recover dried olives which become rich in water-soluble antioxidants and whose water content is 1–20% by weight, for example. Preferably, the drying is performed so as to obtain dried olives whose water content is 5–10% by weight. Thus, only the formation of two phases, the lipid fraction enriched with antioxidants and the oil cake, is favoured during the pressing step.

It also is possible to freeze-dry the ground olives at a reduced pressure of $10^{-3}$–$10^{-1}$ bar or in a vacuum oven at a reduced pressure of 0.1–0.2 bar, for example.

The dried olives may be heated and kept at a high temperature for a certain period of time, before carrying out the pressing, so as to increase the antioxidant content of the lipid fraction.

The dried olives are pressed so as to recover a lipid fraction enriched with antioxidants and an oil cake. This pressing can be carried out at room temperature or at high temperature in a piston press equipped with a filtering cage, especially a CARVER type press marketed by the company Fred S. Carver, Menomonee Falls, Wis. U.S.A, so as to press and to filter in a single step.

Then, at least one extraction is performed on the oil cake at high temperature with MCT or with a $C_2$–$C_6$ alkyleneglycol using a pressure greater than or equal to 40 bar. At least one extraction may be performed on the oil cake in an MCT or $C_2$–C6 alkyleneglycol/oil cake weight ratio of 0.5 to 2, for example. The high temperature extractions may be performed in a piston press equipped with a CARVER type filtering cage.

The alkyleneglycol may be glycol, 1,2-propyleneglycol or 1,3-butyleneglycol, for example.

During an extraction at high temperature with MCT by pressing, the fat-soluble antioxidants are mainly isolated and during an extraction at high temperature with a $C_2$–$C_6$ alkyleneglycol by pressing, the fat-soluble antioxidants and the water-soluble antioxidants are isolated.

EXAMPLES

The present invention is described in greater detail in the non-limiting examples below. In these examples, the percentages are given by weight, unless stated otherwise.

Example 1

1 kg of frozen green olives whose overall water content is 55% by weight is ground with the aid of the ALPINA grinder, marketed by the company C. Hoegger and Cie AG, Gossau, CH- St Gall.

These ground green olives are dried in a vacuum oven of the INOX MAURER 20 type, marketed by the company Inox Maurer AG, Trimbach, CH-Soleure, at a temperature of 55° C. and at a reduced pressure of 0.1 bar, so as to obtain dried green olives whose overall water content is 6% by weight.

Next, these dried green olives are pressed at room temperature in a piston press of the Carver type, at 500 bar for 60 min, so as to recover a lipid fraction enriched with antioxidants and an oil cake.

Next, 50 g of the oil cake thus recovered are extracted at high temperature with 1,2-propyleneglycol. To do this, 50 g of 1,2-propyleneglycol are added to the 50 g of oil cake. The whole is left stirring for 60 min at 80° C., and then the mixture is pressed in a piston press of the CARVER type, at 500 bar for 60 min.

An antioxidant-enriched extract is recovered. The RANCIMAT test at 110° C., in various fats and oils, gives the antioxidant power in the form of antioxidant values indicated in Table I below.

The antioxidant value is defined as the ratio: induction time (sample: extract+oil)/induction time (oil).
RANCIMAT Oxidation Test at 110° C.

The sample is placed in a closed reactor. The sample is heated at 110° C. and is saturated with oxygen derived from air introduced into the reactor. During the oxidation, the reactor is itself connected by a flexible tube to a container containing distilled water and in which a platinum electrode is immersed. The volatile compounds cause an increase in the conductivity. The conductivity is measured and the induction periods are calculated. The induction time is calculated graphically from the plotted curve of the conductivity as a function of time by intersection of the tangent to the curve with the time axis.

Comparative Example i

The procedure is carried out as described in Example 1, except for the fact that 50 g of the oil cake recovered are extracted at high temperature by the organic route, with 85% ethanol.

To do this, 100 ml of 85% ethanol are added to the 50 g of oil cake. The whole is left stirring for 60 min at 80° C. and filtered, before being concentrated to 50% of the volume. Next, 50 g of propyleneglycol are added, the ethanol is evaporated and the residue is centrifuged for 10 min at 3000 rpm, so as to clarify it.

An extract containing the antioxidants is recovered. The RANCIMAT test at 110° C. in various fats and oils gives the antioxidant power in the form of antioxidant values indicated in Table I.

TABLE I

For the RANCIMAT test, the measurements are carried out in the presence of 2% extract relative to chicken fat or relative to olive oil.

| Examples | RANCIMAT test/110° C. (antioxidant value) | |
|---|---|---|
| | Olive oil | Chicken fat |
| 1 | 3.8 | 8.6 |
| 1 | 4.5 | 9.9 |

The Table I antioxidant values, which indicate antioxidant power, show the quality and oxidative stability of the extract obtained using the process according to the present invention (Example 1). This quality and this oxidative stability are comparable to those obtained for an extract obtained using a more complex process, in which an extraction is performed at high temperature by the organic route (Example i).

Example 2

The procedure is carried out in the manner described in Example 1, except for the fact that the measurements for the RANCIMAT test are carried out in the presence of 1% extract relative to chicken fat or relative to olive oil.

Moreover, the antioxidant power is measured in the form of an antioxidant value by the oxygen electrode method at 30° C. in maize oil. These measurements are carried out in the presence of 1% extract relative to maize oil.

Furthermore, the induction time for the lipid fraction recovered after pressing dried green olives at room temperature is measured by the RANCIMAT test at 120° C. The value of the induction time for the lipid fraction is stated in Table III.
Oxidation Test: Oxygen Electrode at 30° C.

An emulsion is prepared by mixing 5% oil and the indicated percentage of antioxidants relative to the oil in a buffer solution of pH 7 (No. 9477, Merck, Darmstadt, D) with 0.1% emulsifier by vigorously stirring under nitrogen for 30 min which is emulsified by 6 consecutive passages at 30° C. in an H 5000 microfluidizer.

The oxidative stability of the emulsion is then measured with the aid of a TRI OX EO 200 electrode coupled with an OXI 530 oxygen meter.

A period of 5 to 10 min is allowed to elapse until the percentage saturation of oxygen has a constant value.

The measurement is carried out at 30° C., with stirring in a closed vessel, after addition of 5 ml of HEMIN catalyst (Fluka AG, Buchs, CH) to 100 ml of emulsion. The HEMIN catalyst is prepared from 52 mg of HEMIN catalyst in 100 ml of water, to which 8 drops of 10% KOH are added. The induction time represents the duration, in hours, for total absorption of the dissolved oxygen. The RANCIMAT at 110° C. in various fats and oils and the oxygen electrode method at 30° C. in maize oil give the antioxidant power in the form of antioxidant values indicated in Table II.

Comparative Example ii

The procedure is carried out in the manner described in Example 2, except for the fact that the ground green olives are not dried.

The RANCIMAT test at 110° C. in chicken fat or in olive oil, and the oxygen electrode method at 30° C. in maize oil give the antioxidant power in the form of antioxidant values indicated in Table II.

The value of the induction time at 120° C. for the lipid fraction is stated in Table III.

Example 3

The procedure is carried out in the manner described in Example 1, except for the fact that the dried olives are preheated at 70° C. for 60 min before being pressed.

After cooling at room temperature, the pressing is performed at room temperature in a piston press of the CARVER type at 500 bar for 60 min. A lipid fraction enriched with antioxidants and an oil cake are recovered.

The induction time for the lipid fraction is measured by means of the RANCIMAT test at 120° C. The value of the induction time for the lipid fraction is stated in Table III below.

Moreover, 50 g of the oil cake recovered are extracted at high temperature with 1,2-propyleneglycol. To do this, 50 g of 1,2-propyleneglycol are added to the 50 g of oil cake. The whole is kept stirring for 60 min at 80° C. and the mixture is pressed in a piston press of the CARVER type, at 500 bar for 60 min.

An extract enriched with antioxidants is recovered.

The RANCIMAT test at 110° C. in chicken fat or in olive oil, and the oxygen electrode method at 30° C. in maize oil give the antioxidant power in the form of antioxidant values indicated in Table II.

Example 4

The procedure is carried out in the manner described in Example 2, except for the fact that 50 g of the oil cake recovered are extracted at high temperature with MCT.

To do this, 50 mg of MCT are added to the 50 g of oil cake. The whole is left stirring for 60 min at 80° C. and the mixture is pressed in a piston press of the CARVER type, at 500 bar for 60 min.

An extract enriched with antioxidants is recovered.

The RANCIMAT test at 110° C. in chicken fat or in olive oil, and the oxygen electrode method at 30° C. in maize oil give the antioxidant power in the form of antioxidant values indicated in Table II.

Comparative Example iv

The procedure is carried out in the manner described in Example 4, except for the fact that the ground green olives are not dried.

The RANCIMAT test at 110° C. in chicken fat or in olive oil, and the oxygen electrode method at 30° C. in maize oil give the antioxidant power in the form of antioxidant values indicated in Table II.

Example 5

The procedure is carried out in the manner described in Example 4, except for the fact that the dried green olives are preheated at 70° C. for 60 min before being pressed.

After cooling at room temperature, the pressing is performed at room temperature in a piston press, of the CARVER type, at 500 bar for 60 min. A lipid fraction enriched with antioxidants and an oil cake are recovered.

The induction time is measured by means of the RANCIMAT test at 120° C. from 1% lipid fraction thus recovered.

Moreover, 50 g of the oil cake recovered are extracted at high temperature with MCT. To do this, 50 g of MCT are added to the 50 g of oil cake. The whole is kept stirring for 60 min at 80° C. and the mixture is pressed in a piston press of the CARVER type, at 500 bar for 60 min.

An extract enriched with antioxidants is recovered.

The RANCIMAT test at 110° C. in chicken fat or in olive oil, and the oxygen electrode method at 30° C. in maize oil give the antioxidant power in the form of antioxidant values indicated in Table II.

TABLE II

All the measurements are performed in the presence of 1% of 1% extract relative to maize oil, relative to chicken fat or relative to olive oil.

| Examples | RANCIMAT test/110° C. (antioxidant value) | | Oxygen electrode test/30° C. (antioxidant value) |
|---|---|---|---|
| | chicken fat | olive oil | maize oil |
| 2 | 4.3 | 2.1 | 7.8 |
| ii | 1.8 | 1.1 | 1.5 |
| 3 | 3.9 | 1.6 | 8.4 |
| 4 | 3.2 | 1.3 | — |
| iv | 1.2 | 1 | — |
| 5 | 1.9 | 1.2 | — |

—: not tested

The antioxidant values, which indicate antioxidant power, respectively in Examples 2 and ii and in Examples 4 and iv in Table II, show an increase in the oxidative stability of the antioxidant-enriched extract obtained from the oil cake, in the case where the ground green olives are dried.

Furthermore, the antioxidant values, which indicate antioxidant power, respectively in Examples 2 and 3 and in Examples 4 and 5 in Table II, show that if the dried green olives are pressed at high temperature, the extract enriched with antioxidants, from the oil cake, has a lower oxidative stability.

Finally, the antioxidant values obtained for Examples 2 and 3 in the oxygen electrode test show the quality and the oxidative stability of the antioxidant compounds in emulsion, compared with the results obtained in an oil in the RANCIMAT oxidation test.

TABLE III

| Examples | RANCIMAT test/120° C. (induction time in hours) |
|---|---|
| 2 | 25 |
| ii | 11 |
| 3 | 42 |

The Table III induction times, which indicate antioxidant power, show that if the dried green olives are preheated before pressing at room temperature, the lipid fraction enriched with antioxidants has an increased oxidative stability.

Example 6

The procedure is carried out in the manner described in Example 2, except for the fact that the olives are ripe olives.

The RANCIMAT test at 110° C. in chicken fat and the oxygen electrode method at 30° C in maize oil give the antioxidant power in the form of antioxidant values indicated in Table IV.

Comparative Example vi

The procedure is carried out in the manner described in Example ii, except for the fact that the olives are ripe olives.

The RANCIMAT test at 110° C. in chicken fat and the oxygen electrode method at 30° C. in maize oil give the antioxidant power in the form of antioxidant values indicated in Table IV.

Example 7

The procedure is carried out in the manner described in Example 4, except for the fact that the olives are ripe olives.

The RANCIMAT test at 110° C. in chicken fat and the oxygen electrode method at 30° C. in maize oil give the antioxidant power in the form of antioxidant values indicated in Table IV.

Comparative Example vii

The procedure is carried out in the manner described in Example iv, except for the fact that the olives are ripe olives.

The RANCIMAT test at 110° C. in chicken fat and the oxygen electrode method at 30° C. in maize oil give the antioxidant power in the form of antioxidant values indicated in Table IV.

TABLE IV

All the measurements are carried out in the presence of 1% extract relative to maize oil or relative to chicken fat.

| Examples | RANCIMAT test/110° C. (antioxidant value) Chicken fat | Oxygen electrode test/30° C. (antioxidant value) Maize oil |
|---|---|---|
| 6 | 1.8 | 1.9 |
| vi | 1.2 | 1.7 |
| 7 | 1.1 | 1.3 |
| vii | 1 | 1.3 |

The antioxidant values, which indicate antioxidant power, respectively in Examples 6 and vi and in Examples 7 and vii in Table IV, show an increase in the oxidative stability of the antioxidant-enriched extract obtained from the oil cake, in the case where the ripe and previously ground olives are dried.

Example 8

A commercial non-virgin olive oil (OLIO SASSO) is stabilized with an olive extract enriched with antioxidants which is prepared in accordance with Example 1.

2 g of the extract are added to 100 g of olive oil and an oil is obtained which is 3.8 times more protected than the oil without the extract by the measurement of the antioxidant power in the form of an antioxidant value in the RANCIMAT test at 110° C.

Example 9

A pesto sauce containing antioxidant-enriched extract, as obtained in Example 4, is prepared.

To do this, a mixture for the pesto sauce is prepared, with stirring at room temperature, containing, per kg of sauce, 463.5 g of a mixture of olive oil and sunflower oil, 165 g of basil, 164 g of grated parmesan, 73 g of whey powder, 72.5 g of parsley, 45 g of ground pignons, 7 g of salt, 8 g of freeze-dried garlic and 2 g of ground white pepper.

2% of antioxidant-enriched extract is then added to this mixture while stirring so as to distribute the extract homogeneously in the pesto sauce thus prepared.

This pesto sauce is then packaged in plastic tubs of 100 g which are then stored at 4–7° C.

Example 10

A pesto sauce containing an antioxidant-enriched lipid fraction, as obtained in Example 3, is prepared.

To do this, a mixture for the pesto sauce is prepared, with stirring at room temperature, containing, per kg of sauce, 233.5 g of lipid fraction enriched with antioxidants, 230 g of sunflower oil, 165 g of basil, 164 g of grated parmesan, 72.5 g of whey powder, 45 g of ground pignons, 7 g of salt, 8 g of freeze-dried garlic and 2 g of ground white pepper.

This pesto sauce is then packaged in plastic tubs of 100 g which are then stored at 4–7° C.

Example 11

A tomato sauce containing an antioxidant-enriched lipid fraction, as obtained in Example 5, is prepared.

To do this, a mixture for the tomato sauce is prepared, with stirring at 50° C., containing, per kg of sauce, 302.4 g of tomato puree, 30 g of lipid fraction enriched with antioxidant, 34.5 g of starch, 17 g of sugar, 2.5 g of freeze-dried onions, 0.9 g of ground white pepper, 8.5 g of salt, 2.5 g of oregano, 0.4 g of finely chopped basil and 601.3 g of water.

The tomato sauce thus prepared is then packaged, at room temperature, in hermetically closed 150 g tins.

Example 12

A tomato sauce containing antioxidant-enriched extract, as obtained in Example 1, is prepared.

To do this, a mixture for the tomato sauce is prepared, with stirring at 50° C., containing, per kg of sauce, 302.4 g of tomato puree, 30 g of sunflower oil, 34.5 g of starch, 17 g of sugar, 2.5 g of freeze-dried onions, 0.9 g of ground white pepper, 8.5 g of salt, 2.5 g of oregano, 0.4 g of finely chopped basil and 601.3 g of water.

2% of antioxidant-enriched extract is then added to this mixture while stirring so as to distribute the extract homogeneously in the tomato sauce thus prepared.

The tomato sauce thus prepared is then packaged, at room temperature, in hermetically closed 150 g tins.

What is claimed is:

1. A process for isolating antioxidant compositions from olives comprising grinding olives to obtain ground olive material, drying the ground olive material under reduced-pressure vacuum conditions to reduce the water content of the olive material to obtain dried olive material and pressing the dried olive material and recovering and obtaining, from the pressing, a composition, which comprises lipids and antioxidant substances, separate from pressed olive cake material.

2. A process according to claim 1 further comprising combining an extraction substance selected from the group consisting of medium-chain triglycerides, of glycol and of a $C_2$–$C_6$ alkyleneglycol with the pressed olive cake material and with the combined extraction substance and cake material at a temperature higher than room temperature, pressing the combined extraction substance and cake material under a pressure of at least 40 bar and recovering and obtaining, from the pressing, an extract separate from the further pressed cake material.

3. A process according to claim 2 wherein the extraction substance is a member selected from the group consisting of glycol and of a $C_2$–$C_6$ alkyleneglycol.

4. A process according to claim 3 wherein the extraction substance is a $C_2$–$C_6$ alkyleneglycol and is selected from the group consisting of 1,2-propyleneglycol and 1,3-butyleneglycol.

5. A process according to claim 2 wherein the extraction substance and cake material are combined in amounts so that a weight ratio of the extraction substance to the cake is from 0.5 to 2.

6. A process according to claim 2 wherein, during the pressing, the combined extraction substance and cake material are at a temperature of up to 80° C.

7. A process according to claim 1 or 2 wherein, during the pressing, the dried olive material has a temperature greater than ambient temperature.

8. A process according to claim 7 wherein the dried olive material has a temperature of up to 70° C.

9. A process according to claim 1 or 2 wherein the ground olive material is dried at a temperature not higher than 80° C. and to a moisture content of from 1% to 20% by weight.

10. A process according to claim 1 or 2 wherein the ground olive material is dried to a moisture content of from 5% to 10% by weight.

11. A process according to claim 1 or 2 further comprising, prior to grinding the olives, freezing the olives and then grinding the frozen olives to obtain the ground olive material.

12. A process according to claim 1 or 2 further comprising, prior to drying the ground olive material, treating the ground olive material enzymatically to hydrolyze glycosides.

13. A process according to claim 1 or 2 wherein the olives are selected from the group consisting of green olives and ripe olives.

14. The lipid and antioxidant composition which is obtained by the process of claim 1, wherein the composition consists essentially of compositional constituents which are compositional constituents of the olives.

15. The extract which is obtained by the process of claim 2, wherein the extract consists essentially of the extraction substance and of compositional constituents which are compositional constituents of the olives.

16. The lipid and antioxidant composition which is obtained by the process of claim 12, wherein the composition consists essentially of compositional constituents which are compositional constituents of the olives.

17. The extract which is obtained by the process of claim 12, wherein the extract consists essentially of the extraction substance and of compositional constituents which are compositional constituents of the olives.

18. A process for protecting a food product or cosmetic product from oxidation comprising incorporating antioxidant compositions into the food or cosmetic product wherein the antioxidant compositions have been obtained by a process which comprises grinding olives to obtain ground olive material, drying the ground olive material under reduced-pressure vacuum conditions to reduce the water content of the olive material to obtain dried olive material and pressing the dried olive material and recovering and obtaining, from the pressing, a composition, which comprises lipids and antioxidant substances, separate from pressed olive cake material.

19. A process for protecting a food product or cosmetic product from oxidation comprising incorporating antioxidant compositions into the food or cosmetic product wherein the antioxidant compositions have been obtained by a process which comprises:

grinding olives to obtain ground olive material, drying the ground olive material under reduced-pressure vacuum conditions to reduce the water content of the olive material to obtain dried olive material and pressing the dried olive material and recovering and obtaining, from the pressing, a composition, which comprises lipids and antioxidant substances, separate from pressed olive cake material;

combining an extraction substance selected from the group consisting of medium-chain triglycerides, of glycol and of a $C_2$–$C_6$ alkyleneglycol with the pressed olive cake material and with the combined extraction substance and cake material at a temperature higher than room temperature, pressing the combined extraction substance and cake material under a pressure of at least 40 bar and recovering and obtaining, from the pressing, an extract separate pressed from the further cake material; and incorporating the extract into the food or cosmetic product so that the product contains the extract in an amount of from 0.5% to 4% by weight.

20. A process according to claim 19 wherein the is a food product and the food is non-virgin olive oil.

* * * * *

UNITED STATES PATENT AND TRADEMARK OFFICE
CERTIFICATE OF CORRECTION

PATENT NO. : 6,309,652 B1
DATED : October 30, 2001
INVENTOR(S) : Aeschbach et al.

Page 1 of 1

It is certified that error appears in the above-identified patent and that said Letters Patent is hereby corrected as shown below:

<u>Title page,</u>
OTHER PUBLICATIONS, add the following publication:
-- Uzzan, Manuel des Corps Gras, ISBN2-85206-662/9, pp. 763-68, 1992 --.

<u>Column 10,</u>
Line 37, after "wherein the" insert -- product --.

Signed and Sealed this

Nineteenth Day of March, 2002

*Attest:*

JAMES E. ROGAN
*Director of the United States Patent and Trademark Office*

*Attesting Officer*